US009333045B2

(12) United States Patent  (10) Patent No.: US 9,333,045 B2
Cooper et al.  (45) Date of Patent: May 10, 2016

(54) METHOD AND MEANS FOR TRANSFERRING CONTROLLER MOTION FROM A ROBOTIC MANIPULATOR TO AN ATTACHED INSTRUMENT

(71) Applicant: Intuitive Surgical Operations, Inc., Sunnvale, CA (US)

(72) Inventors: Thomas Cooper, Menlo Park, CA (US); Anthony McGrogan, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 14/868,178

(22) Filed: Sep. 28, 2015

(65) Prior Publication Data

US 2016/0015463 A1  Jan. 21, 2016

Related U.S. Application Data

(63) Continuation-in-part of application No. 13/710,340, filed on Dec. 10, 2012, now Pat. No. 9,144,467, which is a continuation-in-part of application No. 12/060,104, filed on Mar. 31, 2008, now Pat. No. 8,333,755.

(51) Int. Cl.
*A61B 19/00* (2006.01)
*A61B 17/00* (2006.01)

(52) U.S. Cl.
CPC ............ *A61B 19/2203* (2013.01); *A61B 19/20* (2013.01); *A61B 2017/00477* (2013.01); *A61B 2019/2242* (2013.01)

(58) Field of Classification Search
USPC ...................... 74/490.04, 490.06; 606/1, 130
See application file for complete search history.

(56) References Cited

U.S. PATENT DOCUMENTS 4,919,112 A  4/1990  Siegmund
5,185,508 A  2/1993  Perkinson, III
(Continued)

FOREIGN PATENT DOCUMENTS

WO  WO-200546500 A1  5/2005

OTHER PUBLICATIONS

PCT/US09/38551 International Search Report and Written Opinion of the International Searching Authority, mailed Sep. 1, 2009, 9 pages.

(Continued)

*Primary Examiner* — William Thomson
*Assistant Examiner* — Jeffrey Lipitz

(57) ABSTRACT

A coupler to transfer controller motion from a robotic manipulator to a surgical instrument includes a pin having a tip with a bearing surface and a plate having a driving surface that bears against a gimbal assembly in the surgical instrument. The plate has a surface supported on the bearing surface of the pin. The bearing surface has a center that coincides with an intersection of two rotational axes of the gimbal assembly. The plate is rotated about the center of the bearing surface to transfer controller motion to the surgical instrument. There may be alignment features on the driving surface of the plate to mate with corresponding features on an inner gimbal of the gimbal assembly. An actuator arm may be connected to one side of the plate. An actuator mechanism may be connected to the actuator arm to rotate the plate about the center of the bearing surface.

20 Claims, 4 Drawing Sheets

(56) References Cited

U.S. PATENT DOCUMENTS

| | | |
|---|---|---|
| 5,661,253 A | 8/1997 | Aoki |
| 5,740,699 A | 4/1998 | Ballantyne et al. |
| 6,227,066 B1 | 5/2001 | Stachniak |
| 6,330,837 B1 | 12/2001 | Charles et al. |
| 6,343,072 B1 | 1/2002 | Bechtolsheim et al. |
| 6,346,072 B1 | 2/2002 | Cooper |
| 6,491,701 B2 | 12/2002 | Tierney et al. |
| 8,333,755 B2 | 12/2012 | Cooper et al. |
| 9,144,467 B2 | 9/2015 | Cooper et al. |
| 2006/0199999 A1 | 9/2006 | Ikeda et al. |
| 2008/0065105 A1 | 3/2008 | Larkin et al. |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

METHOD AND MEANS FOR TRANSFERRING CONTROLLER MOTION FROM A ROBOTIC MANIPULATOR TO AN ATTACHED INSTRUMENT

CROSS REFERENCE TO RELATED APPLICATIONS

This application is a continuation of application Ser. No. 13/710,340, filed Dec. 10, 2012, now U.S. Pat. No. 9,144,467, which is a continuation of application Ser. No. 12/060,104, filed Mar. 31, 2008, now U.S. Pat. No. 8,333,755, each of which is hereby incorporated by reference in its entirety.

BACKGROUND

1. Field

Embodiments of the invention relate to the field of mechanical couplers; and more specifically, to couplers for transferring control motion from robotic manipulators.

2. Background

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas and cannula sleeves are passed through small (approximately ½-inch) incisions in the musculature of the patient's abdomen to provide entry ports through which laparoscopic surgical instruments can be passed in a sealed fashion.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by an approximately 12-inch long extension tube, for example, so as to permit the operator to introduce the end effector to the surgical site and to control movement of the end effector relative to the surgical site from outside a patient's body.

In order to provide improved control of the working tools, it may be desirable to control the instrument with a robotic manipulator. The surgeon may operate controls on a console to indirectly manipulate the instrument that is connected to the robotic manipulator. The instrument is detachably coupled to the robotic manipulator so that the instrument can be separately sterilized and selected for use as needed instrument for the surgical procedure to be performed. The instrument may be changed during the course of a surgery.

It is desirable to provide a close coupling between the surgeon's hand movement and the associated instrument movement. Therefore, it is desirable to provide a mechanism for transmitting to controlling motions of a robotic manipulator to a detachable laparoscopic surgical instrument without lost motion or hysteresis.

SUMMARY

A method of transmitting controller motion from a robotic manipulator to a surgical instrument includes rotating a plate included in the robotic manipulator. The plate has a driving surface that bears against an inner gimbal of a gimbal assembly included in the surgical instrument. The plate is rotated about a center of motion that coincides with an intersection of two rotational axes of the gimbal assembly.

The plate has a back surface and an opposing driving surface that bears against a first surface of an inner gimbal of a gimbal assembly of the surgical instrument. The plate includes a pin receiving portion that extends outwardly from the driving surface and away from the back surface. The pin receiving portion includes a spherical receiving surface to receive the spherical bearing surface of a pin having a tip with a spherical bearing surface. The spherical bearing surface is located at a distance above the driving surface such that the center of the spherical bearing surface coincides with an intersection of the gimbal assembly axes of the driven device.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
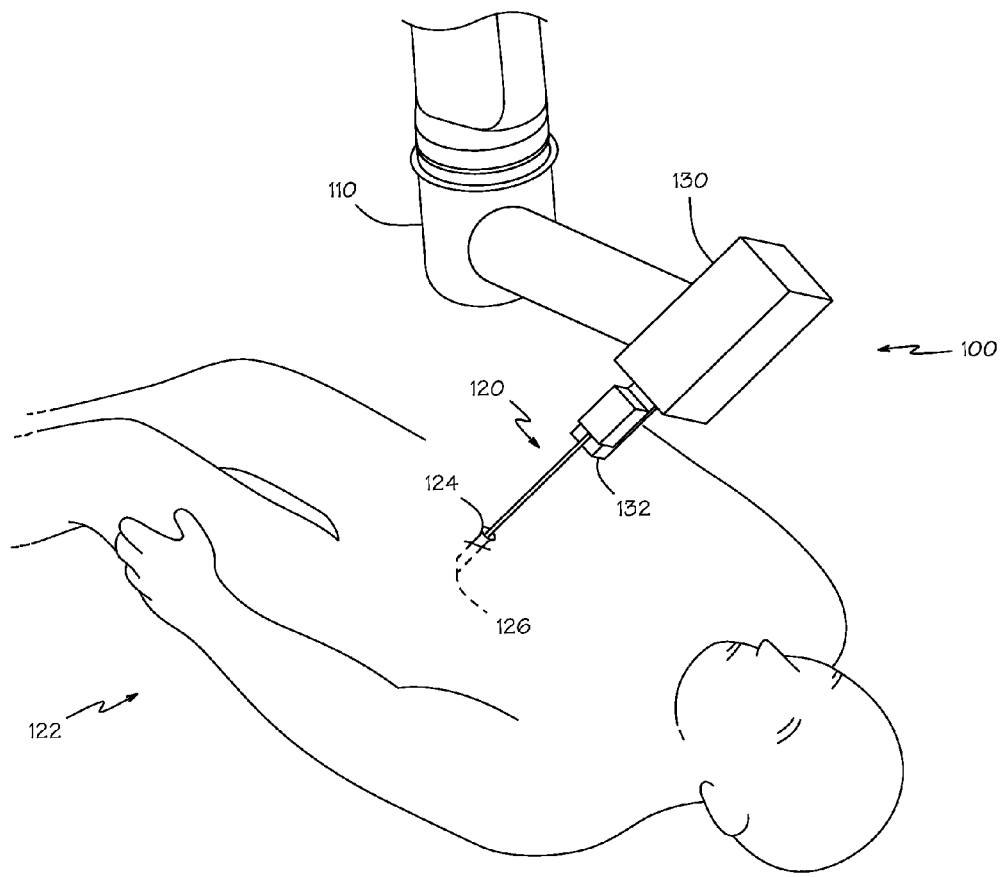
FIG. 1 is a simplified perspective view of a robotic surgical system with a robotically controlled surgical instrument inserted through a port in a patient's abdomen.

FIG. 1 is a simplified perspective view of a robotic surgical system 100, in accordance with embodiments of the present invention. The system 100 includes a support assembly 110 mounted to or near an operating table supporting a patient's body 122. The support assembly 110 enables the delivery of one or more surgical instruments 120 to a surgical site within the patient's body 122.

The term "instrument" is used herein to describe a device configured to be inserted into a patient's body and used to carry out surgical procedures. The instrument may comprise a single surgical tool, such as a needle driver, a cautery device, or a cutting tool, an imaging device (e.g., an endoscope or ultrasound probe), or a combined device that includes a combination of two or more various tools and imaging devices.

The simplified perspective view of the system 100 shows only a single robotic manipulator 130 supporting a single instrument 120 to allow aspects of the invention to be more clearly seen. A functional robotic surgical system would further include a vision system that enables the operator to view the surgical site from outside the patient's body 122. The vision system may comprise, e.g., a video monitor displaying images received by an optical device provided at a distal end of one of the surgical instruments 120. The optical device may comprise, e.g., a lens coupled to an optical fiber which carries the detected images to an imaging sensor (e.g., a CCD or CMOS sensor) outside of the patient's body 122. Alternatively, the imaging sensor may be provided at the distal end of the surgical instrument 120, and the signals produced by the sensor are transmitted along a lead or wirelessly for display on the monitor. An illustrative monitor is the stereoscopic display on the surgeon's cart in the da Vinci® Surgical System, manufactured by Intuitive Surgical, Inc., of Sunnyvale Calif.

A functional robotic surgical system would further include a control system for controlling the insertion and articulation of the support assembly 110 and surgical instruments 120. This control may be effectuated in a variety of ways, depending on the degree of control desired, the size of the surgical assembly, and other factors. In some embodiments, the control system may include one or more manually operated input devices, such as a joystick, exoskeletal glove, or the like. These input devices control servo motors which, in turn, control the articulation of the support assembly 110. The forces generated by the servo motors are transferred via drivetrain mechanisms, which transmit the forces from the servo motors generated outside the patient's body 122 through an intermediate portion of the elongate surgical instrument 120 to a portion of the surgical instrument inside the patient's body 122 distal from the servo motor. The drivetrain mechanism may comprise, e.g., cables in tension, or rods or tubes in compression or under torsion. Persons familiar with telemanipulative surgery will know of systems such as the da Vinci® Surgical System and the Zeus® system originally manufactured by Computer Motion, Inc. and various illustrative components of such systems.

FIG. 1 shows a surgical instrument 120 inserted through an entry guide cannula 124, e.g., a single port in the patient's abdomen. A functional robotic surgical system would provide an entry guide manipulator and an instrument manipulator. The entry guide 124 is mounted onto the entry guide manipulator, which includes a robotic positioning system for positioning the distal end 126 of the entry guide 124 at the desired target surgical site. The robotic positioning system may be provided in a variety of forms, such as, e.g., a serial link arm having multiple degrees of freedom (e.g., six degrees of freedom) or a remote center arm which is positioned by a setup joint mounted onto a base. Alternatively, the entry guide manipulator may be manually maneuvered so as to position the entry guide 124 in the desired location. In some telesurgical embodiments, the input devices that control the manipulator(s) may be provided at a location remote from the patient (outside the room in which the patient is placed). The input signals from the input devices are then transmitted to the control system, which, in turn, manipulates the manipulators 130 in response to those signals. The instrument manipulator is coupled to the entry guide manipulator such that the instrument manipulator 130 moves in conjunction with the entry guide 124.

Figure 2:
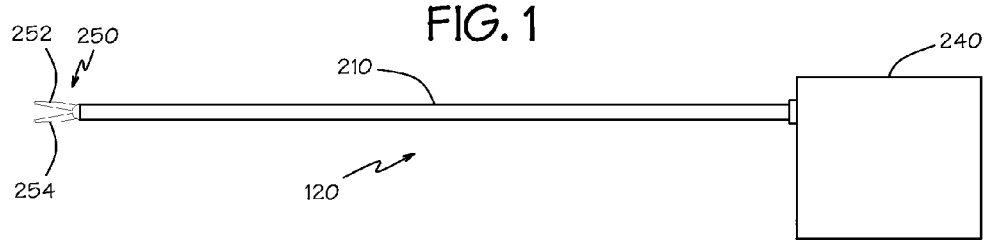
FIG. 2 is a plan view of a surgical instrument for use with a robotic manipulator.

FIG. 2 is a plan view of an illustrative embodiment of the surgical instrument 120, comprising an elongate body portion tube 210, a distal portion 250, and a proximal control mechanism 240. The distal portion 250 of the surgical instrument 120 may provide any of a variety of surgical devices such as the forceps shown, a needle driver, a cautery device, a cutting tool, an imaging device (e.g., an endoscope or ultrasound probe), or a combined device that includes a combination of two or more various tools and imaging devices.

Figure 3:
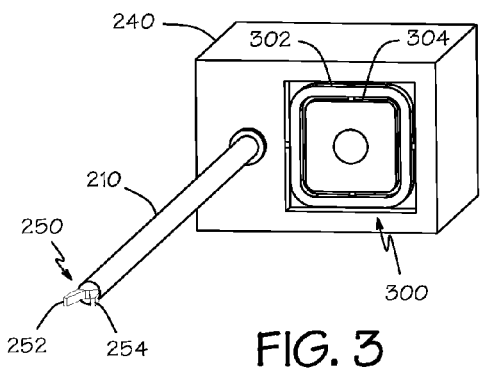
FIG. 3 is a perspective view of the surgical instrument shown in FIG. 2.

FIG. 3 is a perspective view showing the proximal control mechanism 240 of the surgical instrument 120 in more detail. In this embodiment, a gimbal assembly 300 is provided to receive a controlling input. The gimbal assembly includes an outer gimbal 302 that is pivotally supported by a housing of the proximal control mechanism and an inner gimbal 304 that is pivotally supported by the outer gimbal. The axes of the inner and outer gimbal assemblies intersect and allow the inner gimbal assembly to move with two degrees of rotational freedom, one for each of the two axes of the gimbal assembly.

The two degrees of freedom may control two related motions of the surgical tool 250 provided at the distal portion of the surgical instrument 120 or they may control two unrelated motions. For example, rotation of one axis of the gimbal assembly 300 may control the angular position of one of the forceps jaws 252 and rotation of the other axis may control the angular position of the other jaw 254. In another example, rotation of one axis of the gimbal assembly 300 may open and close the forceps jaws 252, 254 and rotation of the other axis may rotate the forceps 250. In other embodiments, more than one gimbal assembly may be provided to control a greater number of movements of the tool provided at the distal portion of the surgical instrument. The additional gimbal assemblies may be adjacent one another or may be provided on other surfaces of the proximal control mechanism 240 of the surgical instrument 120. The surgical instrument is detachably connected to the robotic manipulator 130. The robotic manipulator includes a coupler 132 to transfer controller motion from the robotic manipulator to the surgical instrument 120.

Figure 4:
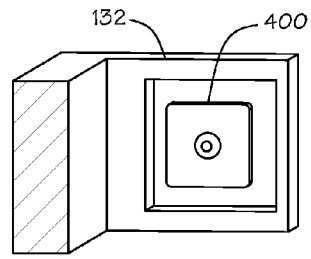
FIG. 4 is a perspective view of a coupler portion of a robotic manipulator that embodies the invention.

FIG. 4 shows a perspective view of the coupler portion 132 of the robotic manipulator 130. The coupler 132 includes a plate 400 that bears against the inner gimbal 304 of the gimbal assembly 300 in the proximal control mechanism 240 of the surgical instrument 120 when the instrument is connected to the robotic manipulator 130.

Figure 5:
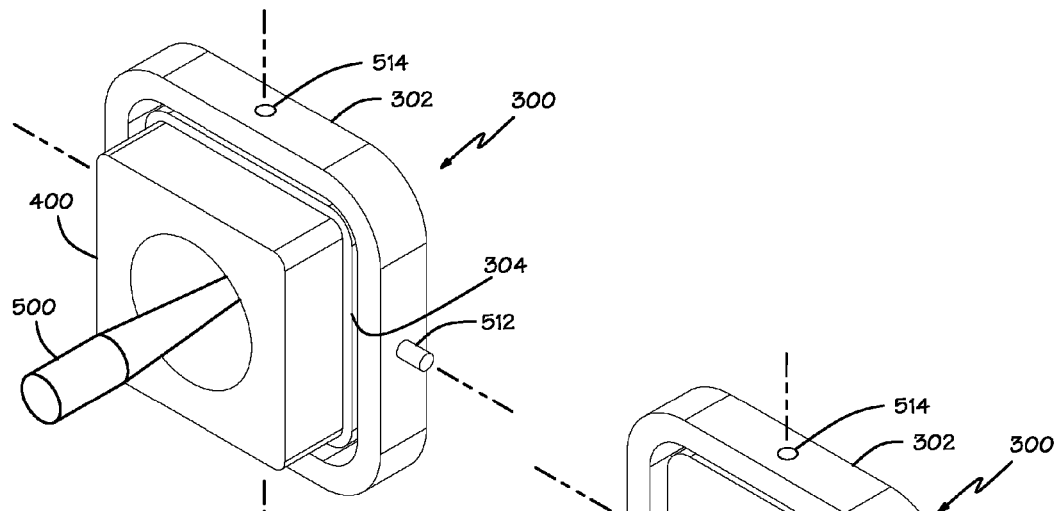
FIG. 5 is a perspective view of a coupler system that embodies the invention in a coupled condition.
Figure 6A:
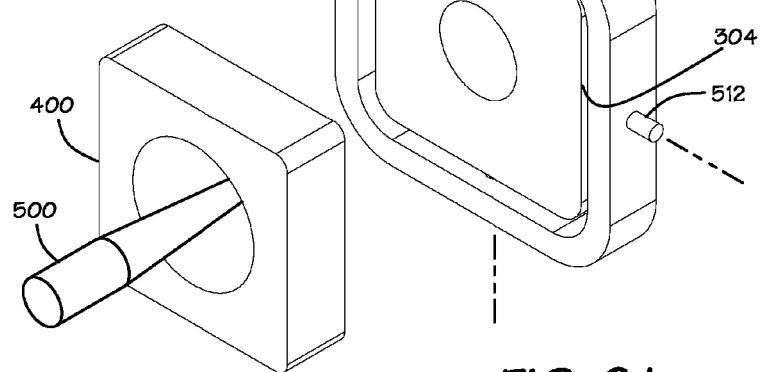
FIG. 6A is a perspective view of the coupler system of FIG. 5 in an uncoupled condition.
Figure 6B:
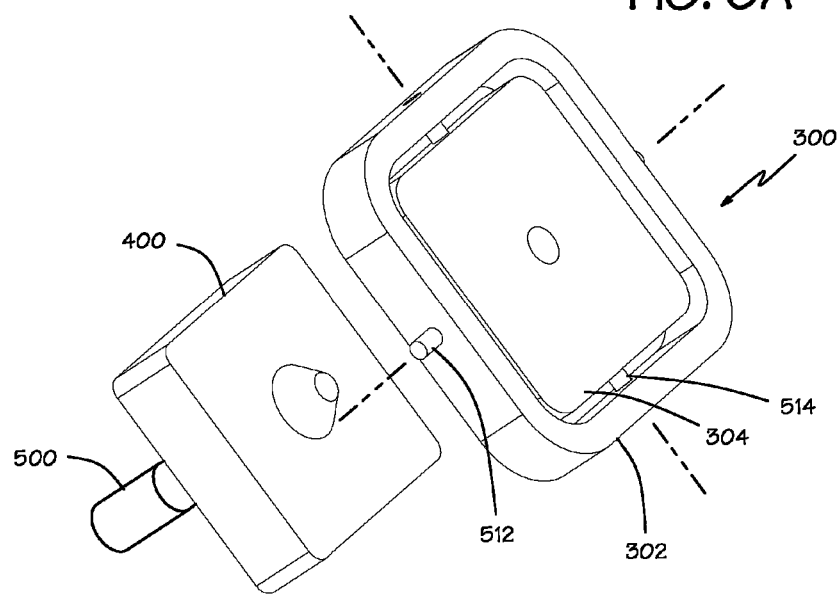
FIG. 6B is a perspective view of the coupler system of FIG. 6A from the opposite side.

FIG. 5 shows a perspective detail of the plate 400 and the gimbal assembly 300 with the plate bearing against a first surface of the inner gimbal 304. FIGS. 6A and 6B shows two perspective views of the plate 400 and the gimbal assembly 300 when the surgical instrument is separated from the robotic manipulator. A pin 500 pivotally supports the plate 400. The inner gimbal 304 is connected by a first set of pivots 514 to the outer gimbal 302. A second set of pivots 512 connect the outer gimbal 302 to the housing of the proximal control mechanism of the surgical instrument. The rotational axes of the two sets of pivots 512, 514 intersect allowing the inner gimbal 304 to rotate with two degrees of freedom.

Figure 7:
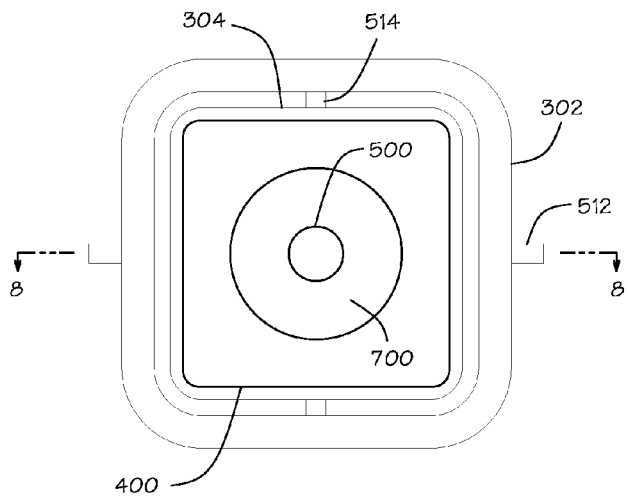
FIG. 7 is a plan view of the coupler system of FIG. 5.
Figure 8A:
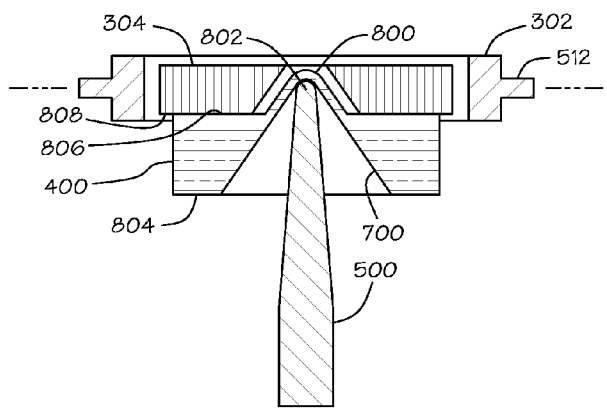
FIG. 8A is a cross section of the coupler system of FIG. 5 taken along line 8-8 in a first operative position.
Figure 8B:
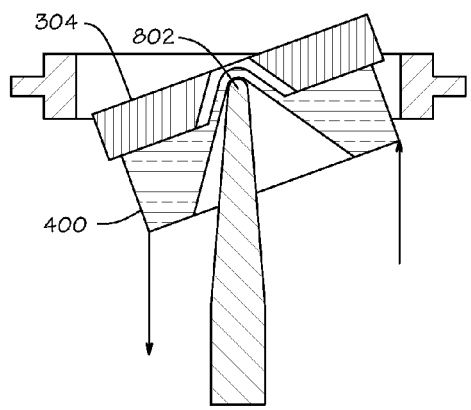
FIG. 8B is a cross section of the coupler system of FIG. 5 taken along line 8-8 in a second operative position.
Figure 8C:
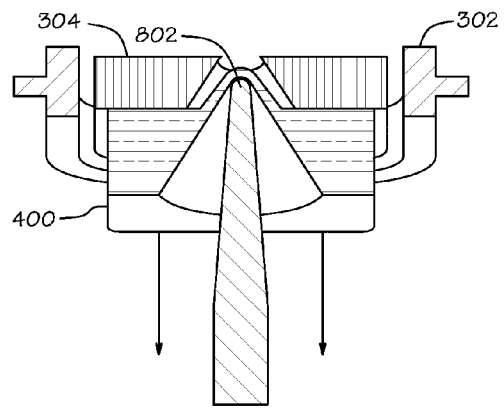
FIG. 8C is a cross section of the coupler system of FIG. 5 taken along line 8-8 in a third operative position.

FIG. 7 is a plan view of the plate 400 and the gimbal assembly 300 with the pin 500 shown to the front. FIGS. 8A, 8B, and 8C are section views taken along line 8-8 in FIG. 7 showing the plate 400 and the gimbal assembly 300 in three different operating positions. As seen in FIG. 8A, the pin 500 may have a tip with a spherical bearing surface 802. The plate 400 is supported on the spherical bearing surface 802 of the pin 500 to provide two degrees of rotational freedom about the center of the spherical bearing surface that coincide with the two degrees of freedom of the inner gimbal 304.

The plate has a back surface 804 and an opposing driving surface 806 that bears against a first surface 808 of the inner gimbal 304. The plate includes a pin receiving portion 800 that extends outwardly from the driving surface 806 and away from the back surface 804. The pin receiving portion 800 may include a spherical receiving surface to receive the spherical bearing surface 802 of the pin 500. The spherical bearing surface is located at a distance above the driving surface 806 such that the center of the spherical bearing surface 802 coincides with an intersection of the gimbal assembly axes. The pin receiving portion 800 includes a conical surface 700 that extends from the spherical bearing surface to the back surface 804.

FIG. 8B shows the application of driving forces as suggested by the arrows that cause the plate 400 to rotate the inner gimbal 304 about its pivots connected to the outer gimbal 302. FIG. 8C shows the application of driving forces as suggested by the arrows that cause the plate 400 to rotate the outer gimbal 302 about its pivots connected to the instrument housing along with the connected inner gimbal 304. There is no relative movement between the plate 400 and the inner gimbal 304 because the plate rotates about the center of the spherical bearing surface 802 which coincides with the intersection of the gimbal assembly 300 axes. It will be appreciated that other arrangements may be used to support the plate with two degrees of rotational freedom about a center that coincides with the two degrees of freedom of the inner gimbal 304. For example, a pin with a socket may support a plate that includes a spherical bearing surface that is supported by the socket.

Figure 9:
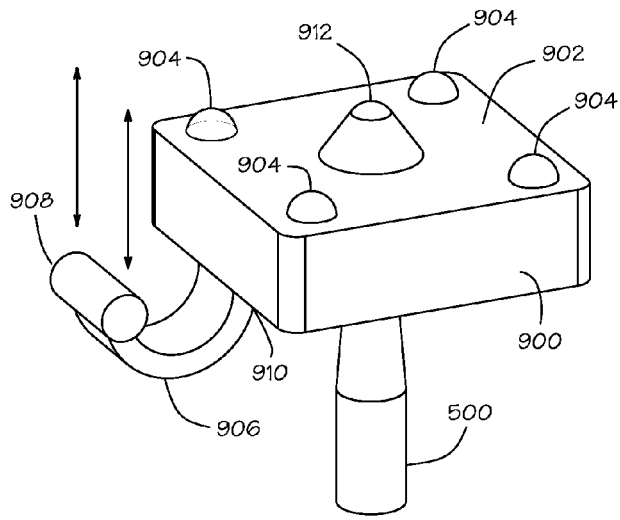
FIG. 9 is a perspective view of a block that shows another embodiment of the invention.

FIG. 9 shows another embodiment of the plate 900. The plate includes a plurality of alignment features 904 on the driving surface 902 to mate with corresponding features on the first surface of the inner gimbal. Since the plate may be relative unconstrained when it is not bearing against the inner gimbal, the alignment features 904 may provide a known alignment between the plate 900 and the gimbal assembly to provide a predictable control motion to be coupled from the plate to the gimbal assembly. While the plurality of alignment features are shown as a raised hemispherical surface, other shapes may be used such as a depressed hemispherical surface, conical surfaces, pyramidal surfaces, and the like. The plurality of alignment features may be of differing shapes and/or sizes.

The embodiment of the plate 900 shown in FIG. 9 further includes an actuator arm 906 connected to one side of the plate at a first end 910 of the arm. It will be appreciated that other embodiments may use the alignment features or the actuator arm without the other. An actuator mechanism may be coupled to the actuator arm 906 adjacent a second end 908 of the actuator arm opposite the first end. The actuator mechanism may rotate the plate 900 about the center of the spherical bearing surface in the two degrees of freedom as suggested by the two double ended arrows. It will be appreciated that the plate can be moved with two degrees of freedom by two linear actuators operating on opposing sides of the second end 908 of the actuator arm 906.

Figure 10:
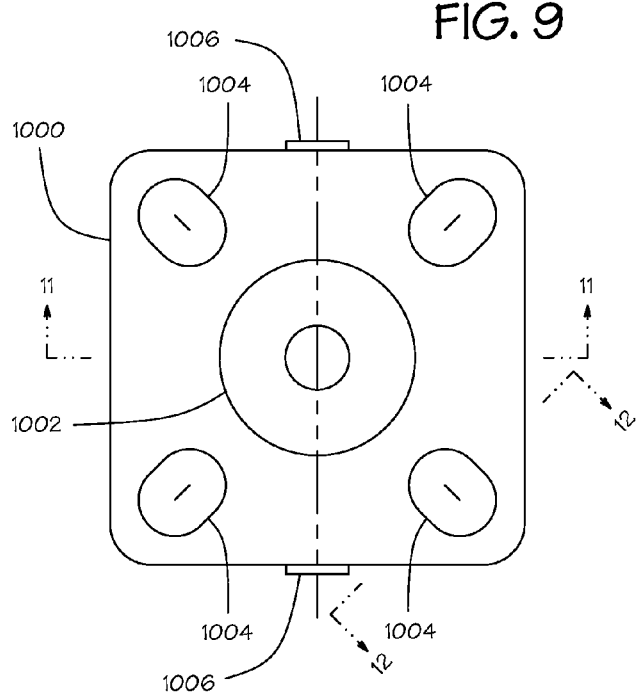
FIG. 10 is a plan view of an inner gimbal that shows another embodiment of the invention.
Figure 11:
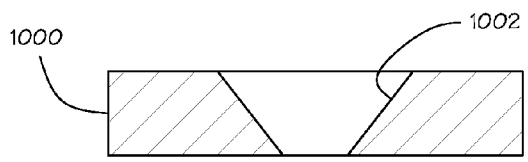
FIG. 11 is a cross section of the inner gimbal of FIG. 10 taken along line 11-11.
Figure 12:
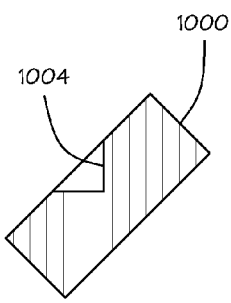
FIG. 12 is a cross section of the inner gimbal of FIG. 10 taken along line 12-12.

FIG. 10 shows a plan view of an inner gimbal 1000 that may be used in an embodiment of the invention. As may be seen in the section view of FIG. 11 taken along line 11-11 of FIG. 10, the inner gimbal 1000 may provide a recess 1002, such as a hole with straight or sloping sides, to receive a pin receiving portion 912 of a cooperating plate 900 as shown in FIG. 9. In one embodiment a raised hemispherical surface 904 on one part mates with an elongated V-shaped groove 1004 on the inner gimbal best seen in the section view of FIG. 12 taken along line 12-12 of FIG. 10. This arrangement may accommodate differences in the spacing of the alignment features while still providing a stiff connection.

Embodiments of the inventive coupler may provide an automatic alignment between the two parts when they are brought together. The driver and the instrument may match in angle when coupled so that the orientation of the distal surgical tool 250 is determined by the coupling. This may allow the manipulator 130 and the instrument 120 to be brought to a known position and connected without causing the distal surgical tool 250 to move during the coupling process. The instrument 120 may be removed from the manipulator 130 with the gimbal 304 at an angle because the pin receiving portion 800 and the alignment features 904 may be shaped to permit separation by moving the instrument away from the manipulator with a variety of relative motions.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A coupler to transfer controller motion from a robotic manipulator to a surgical instrument, the coupler comprising:
a pin having a tip with a bearing surface; and
a plate having a driving surface that bears against a gimbal assembly included in the surgical instrument, the plate including a pin receiving portion having a receiving surface supported on the bearing surface of the pin, the bearing surface having a center that coincides with an intersection of two rotational axes of the gimbal assembly, the plate being rotated about the center of the bearing surface.

2. The coupler of claim 1 wherein the pin receiving portion includes a conical surface that extends from the bearing surface through the driving surface to a back surface of the plate.

3. The coupler of claim 1 further including a plurality of alignment features on the driving surface of the plate to mate with corresponding features on an inner gimbal of the gimbal assembly of the surgical instrument.

4. The coupler of claim 3 wherein the plurality of alignment features include a raised hemispherical surface.

5. The coupler of claim 3 wherein the plurality of alignment features include V-shaped groove.

6. The coupler of claim 1 further including an actuator mechanism to rotate the plate about the center of the bearing surface.

7. The coupler of claim 6 further including an actuator arm connected to one side of the plate at a first end of the actuator arm, wherein the actuator mechanism is coupled to the actuator arm adjacent a second end of the actuator arm opposite the first end.

8. A method of transmitting controller motion from a robotic manipulator to a surgical instrument, the method comprising rotating a plate included in the robotic manipulator, the plate having a driving surface that bears against a gimbal assembly included in the surgical instrument, the plate being supported on a bearing surface of a pin that extends outwardly from the driving surface, the bearing surface having a center that coincides with an intersection of two rotational axes of the gimbal assembly, the plate being rotated about the center of the bearing surface.

9. The method of claim 8 wherein a plurality of alignment features on the driving surface of the plate are mated with corresponding features on the gimbal assembly of the surgical instrument.

10. The method of claim 9 wherein the plurality of alignment features includes a raised hemispherical surface, and the corresponding features include a V-shaped groove.

11. The method of claim 9 wherein the plurality of alignment features includes a V-shaped groove, and the corresponding features include a raised hemispherical surface.

12. The method of claim 8 further comprising controlling an actuator mechanism to rotate the plate.

13. The method of claim 12 wherein the actuator mechanism is coupled to a first end of an actuator arm that is connected to one side of the plate at a second end of the actuator arm opposite the first end.

14. A robotic surgical system comprising:
a surgical instrument, the surgical instrument including a gimbal assembly at a first end operatively coupled to a surgical tool at a second end opposite the first end;
a robotic manipulator detachably connected to the surgical instrument, the robotic manipulator including a coupler to transfer controller motion from the robotic manipulator to the surgical instrument, the coupler including a pin having a tip with a bearing surface; and
a plate having a driving surface that bears against the gimbal assembly included in the surgical instrument, the plate including a pin receiving portion having a receiving surface supported on the bearing surface of the pin, the bearing surface having a center that coincides with an intersection of two rotational axes of the gimbal assembly, the plate being rotated about the center of the bearing surface.

15. The robotic surgical system of claim 14 wherein the pin receiving portion includes a conical surface that extends from the bearing surface through the driving surface to a back surface of the plate.

16. The robotic surgical system of claim 14 wherein of the plate of the coupler further includes a plurality of alignment features on the driving surface to mate with corresponding features on an inner gimbal of the gimbal assembly of the surgical instrument.

17. The robotic surgical system of claim 16 wherein the plurality of alignment features include a raised hemispherical surface.

18. The robotic surgical system of claim 16 wherein the plurality of alignment features include a V-shaped groove.

19. The robotic surgical system of claim 14 wherein the robotic manipulator further includes an actuator mechanism to rotate the plate about the center of the bearing surface.

20. The robotic surgical system of claim 19 wherein the plate of the coupler further includes an actuator arm connected to one side of the plate at a first end of the actuator arm, wherein the actuator mechanism is coupled to the actuator arm adjacent a second end of the actuator arm opposite the first end.

* * * * *